United States Patent [19]

Abts

[11] Patent Number: 4,773,267
[45] Date of Patent: Sep. 27, 1988

[54] ULTRASONIC SENSING

[75] Inventor: Leigh R. Abts, Barrington, R.I.

[73] Assignee: Micro Pure Systems, Inc., R.I.

[21] Appl. No.: 360,404

[22] Filed: Mar. 22, 1982

Related U.S. Application Data

[63] Continuation-in-part of Ser. No. 136,169, Mar. 31, 1980, abandoned.

[51] Int. Cl.[4] .............................................. G01N 24/00
[52] U.S. Cl. ........................................ 73/597; 73/599
[58] Field of Search ................. 73/597, 599, 627, 629, 73/632, 642

[56] References Cited

U.S. PATENT DOCUMENTS

| | | | |
|---|---|---|---|
| 2,755,662 | 7/1956 | Swengel | 73/599 |
| 2,949,769 | 8/1960 | Heller | 73/67.6 |
| 3,230,504 | 11/1962 | Horan et al. | 340/10 |
| 3,245,251 | 4/1966 | Ardenne | 73/67.9 |
| 3,346,065 | 10/1967 | Bourquard | |
| 3,427,867 | 2/1969 | Nute et al. | 73/67.9 |
| 3,553,636 | 1/1971 | Baird | 340/1 |
| 3,618,696 | 11/1971 | Hurwitz | 181/0.5 |
| 3,666,979 | 5/1972 | McElroy | 310/9.6 |
| 3,774,444 | 11/1973 | Kent | 73/67.6 |
| 3,914,984 | 10/1975 | Wade | 73/61 |
| 3,934,460 | 1/1976 | Sherwin et al. | 73/71.5 |
| 3,950,660 | 4/1976 | McElroy | 310/9.1 |
| 3,973,430 | 8/1976 | Cirulis et al. | 73/61.1 |
| 3,974,631 | 8/1976 | Namery | 76/67.5 |
| 3,974,684 | 8/1976 | Roule et al. | 73/642 |
| 4,068,521 | 1/1978 | Cosentino et al. | 73/19 |
| 4,080,837 | 3/1978 | Alexander et al. | 73/597 |
| 4,166,394 | 9/1979 | Figura | 73/597 |
| 4,202,215 | 5/1980 | Meyer | 73/599 |
| 4,327,587 | 5/1982 | Docekal et al. | 73/590 |

Primary Examiner—Jerry W. Myracle

[57] ABSTRACT

An ultrasonic device in which a concave transducer, partially surrounded by and insulated from a pair of electrically-grounded shields, focuses a signal and directs it to a limited portion of a second lens which further focuses the signal and directs a highly concentrated signal into a fluid, whereby particles therein can be detected with increased sensitivity, and whereby the composition of a homogeneous fluid can be determined by measuring the amount of the attenuation or the sound velocity of ultrasonic pulses therethrough or by comparing the frequency spectrum of the pulse with known spectra.

4 Claims, 2 Drawing Sheets

ULTRASONIC SENSING

This application is a continuation-in-part of U.S. patent application Ser. No. 136,169, filed Mar. 31, 1980, now abandoned.

FIELD OF THE INVENTION

This invention relates to obtaining information about fluids, for example, the existence of very small discontinuities in the fluid or the composition of the fluid, which may be homogeneous.

BACKGROUND OF THE INVENTION

The background of this invention pertaining to the detection of discontinuities in a flowing fluid stream is set out in my U.S. Pat. Nos. 4,112,773 and 4,214,484, both hereby incorporated by reference. The ultrasonic detection devices disclosed in those patents can detect particles in a flow as small as 10 microns in diameter with the same degree of accuracy that the prior art only obtained with particles ten times larger. In both these inventions, a portion of the conduit through which the fluid flows is used as a lens (i.e., the natural curvature of the inside of the conduit acts as the inside face of the lens) to focus the ultrasonic beam. The conduit, however, which may be an already existing pipe section or a specially fabricated one, apparently contain many small flaws throughout, and the flaws will scatter a portion of an ultrasonic beam passing therethrough thereby reducing the overall beam energy. Similarly, metal conduit will have grains, which also will scatter the beam to some degree. This loss of energy is important because the reflected signals from the tiny discontinuities are very small in magnitude to begin with, and scattering and other losses reduce the amount of energy available to be reflected. By the same token, even minor noise levels present a serious problem. However, in the past, the prior art fluid discontinuity detection devices have for the most part disregarded noise problems, and the only ultrasonic detectors even partially protected from noise have been the non-destructive workpiece testing devices, which usually operate in extremely noisy environments, e.g., in close proximity to metal working equipment.

In addition to detecting discontinuities in a standing fluid or in a flow, it is often desirable to be able to determine the composition of the fluid itself. For example, in certain chemical processes, two or more liquid components may be mixed together to form a homogeneous fluid, and the percentages of the components may vary. While the change in the amount of some of the components within certain limits may be acceptable, a minor change in the percentage of a certain component may ruin the entire process. Accordingly, it is important to be able to detect any change in percentages of the components and to identify the component or components which change. This cannot be done with the prior art detection devices, which are limited to dealing either with immiscible liquids (e.g., determining the location of the interface between them) or with solids or slurries in the flow (e.g., measuring the scattering caused by these solids or semi-solids to determine the percentage of solids or semi-solids in the flow).

SUMMARY OF THE INVENTION

I have discovered that discontinuities in fluids can be detected with improved sensitivity when an ultrasonic beam is highly concentrated and also when it is focused prior to reaching a conduit lens thereby reducing the amount of area of the conduit lens and reducing beam energy losses caused by any conduit flaws, grains or other conduit conditions. In addition, the transducer for the detector is at least partially surrounded by a double electrically-grounded shield to reduce noise. Also, I have further discovered that the composition of the fluid can be determined by measuring the amount of attenuation or the velocity of an ultrasonic signal through it or by creating a frequency spectrum for the signal.

In preferred embodiments, a concave transducer is mounted in the bottom of a blind hole in the sidewall of a conduit so as to focus and thereby narrow the ultrasonic beam before it reaches the lens formed by the conduit. Accordingly, the amount of conduit used as a lens is reduced, and correspondingly less of the beam is scattered. In addition, the double focusing arrangement produces a highly concentrated beam, and the transducer is shielded from noise by two electrically-grounded shields.

Also in the preferred embodiment, the composition of a fluid with a number of known components can be determined by measuring the amount of sound absorption at various frequencies or by measuring the sound velocity of the beam through the fluid at different times. In addition, fluid composition information can be obtained by performing a fast Fourier transform or other spectral analysis on an ultrasonic pulse sent through the fluid.

PREFERRED EMBODIMENT

We turn now to the structure and operation of a preferred embodiment, after first briefly describing the drawings.

DRAWINGS

STRUCTURE

Figure 1:
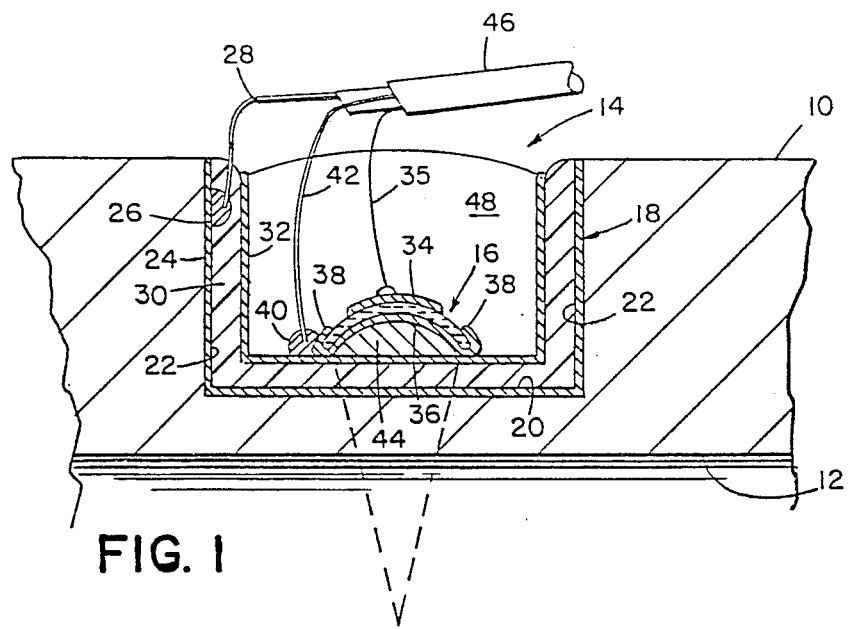
FIG. 1 is an enlarged cross-sectional view of said embodiment.
Figure 2:
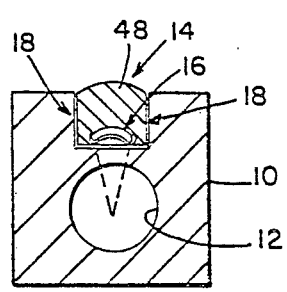
FIG. 2 is a cross-sectional view of said embodiment.

Referring to FIGS. 1-2, there is shown a tube 10 of methyl methacrylate. Tube 10 has an interior bore 12 with a one and a half inch diameter.

Ultrasonic transmitter-receiver 14 includes piezoelectric crystal 16 mounted in blind hole 18. Blind hole 18 has a flat bottom 20 and a cylindrical sidewall 22. Sidewall 22 and bottom 20 are coated with a thin first layer 24 of electrically conductive silver paint. A suitable paint is DuPont Conductor Composition 907770 Butyl Acetate. Conductive epoxy 26 electrically connects a wire 28 to the conductive layer 24. The conductive epoxy 26 is Eccobond Solder 56C. The wire 28 is C21174 from the Cooner Sales Company.

A non-conductive epoxy layer 30 covers all of the first conductive layer 24. Araldite epoxy is suitable for layer 30. A second thin layer 32 of conductive paint covers the epoxy layer 30. First conductive layer 24 and second conductive layer 32 are electrically insulated from each other by epoxy layer 30.

Piezoelectric crystal 16 is attached to the second conductive layer 32 above the bottom 20 of the blind hole 18. Crystal 16 is concave. It has a diameter of ½ inch, and the radius of the concavity is ⅛ inch. Crystal 16 has an upper electrode 34 and a lower electrode 36. Upper electrode 34 is circular and has a diameter of about ⅜ inches. The upper electrode 34 is soldered to wire 35, which is the same type as wire 28. Lower electrode 36 covers the entire lower surface of the crystal 16. A small portion 38 of the lower electrode 36 extends over the outer edge of the upper surface to within 1/32 of an inch of the upper electrode 34. The crystal 16 is a 7.5 MHz crystal, Model PZT5A, available from the Valpey-Fisher Company of Hopkington, Mass. The transducer could also be a flat crystal mounted above a concave lens.

A piece of conductive epoxy 40 electrically connects the portion 38 of the lower electrode 36 to the second conductive layer 32. A wire 42 is also connected to the epoxy 40. Wire 42 and epoxy 40 are the same type as those connected to the first conductive layer 24.

Conductive epoxy 44 fills the concavity between the crystal 16 and the second layer 32, and holds the crystal 16 in place. Stycyst 1970 is a suitable epoxy for this purpose.

Wire 28 from the first layer 24 is connected to the outer ground shield of a lead 46. Wire 42 from the lower electrode 36 is connected to the inner ground shield of the lead 46, and wire 35 from the upper electrode is connected to the hot wire of the lead 46. Lead 46 is Belden 9232 75 ohm triax.

An epoxy backing 48 covers the crystal 16 and fills the remainder of the blind hole 18. The epoxy backing 48 is tungsten-loaded Araldite mixed with a polyamide hardener. The ratio of epoxy to tungsten for the backing 48 is 1:1 by weight.

Figure 3:
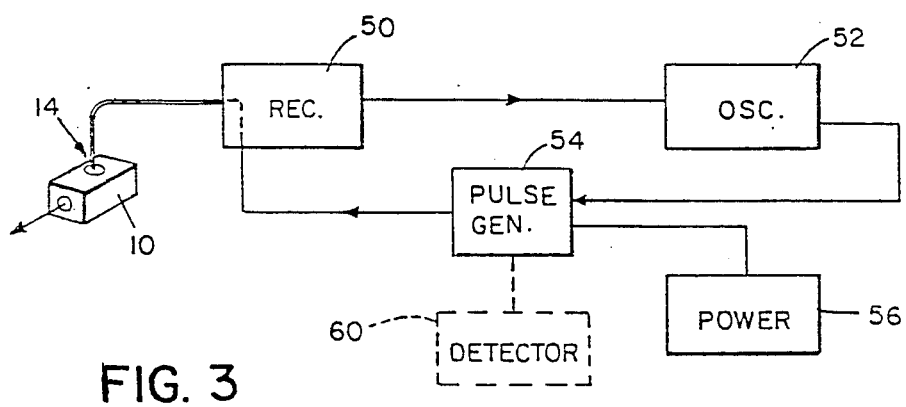
FIG. 3 is a block diagram of the electrical elements of said embodiment.

As shown in FIG. 3, lead 46 is connected to a receiver 50. Receiver 50 is an MCM1100, which is available from Micro Pure Systems, Inc., the assignee herein. The trigger output from the receiver 50 is connected to the trigger input of an oscilloscope 52. The oscilloscope is a Tektronix 465B dual trace scope. The A+ output from the oscilloscope 52 is connected to an input of pulse generator 54. Pulse generator 54 is connected to a power supply 56. A Matec Pulser Receiver R.F. Plug-In Model 755 is a suitable pulse generator, and a Matec Model 6600 Pulse Modulator and Receiver is a suitable power supply. The output of the pulse generator 54 is connected back to the crystal 16 through receiver 50.

OPERATION

In operation, the receiver 50 triggers the oscilloscope 52 which in turn triggers the pulse generator 54. The generator 54 then sends a burst of one pulse to the crystal 16. The pulse energizes the crystal 16, and the crystal transmits an ultrasonic signal into the flow.

This ultrasonic signal is focused three-dimensionally because the crystal 16 is concave. This necessarily narrows the signal and concentrates it as the signal passes into the conduit. The conduit focuses the signal two-dimensionally because of the lens formed by the curvature of the conduit; as explained in my U.S. Pat. No. 4,112,773. However, by first narrowing the signal before it reaches the conduit, the amount of conduit used as the lens is significantly reduced. Almost any conduit has small flaws or other imperfections generally distributed throughout, and metal conduit, in addition, has grains. All of these will scatter ultrasonic energy which strikes them, and such scattered energy is lost from the overall signal. By reducing the area of the conduit used as a lens, the total number of such scatterers in the conduit lens is reduced, thereby reducing the overall amount of energy lost. At the same time, the signal travels through the narrowest part of the conduit thereby reducing absorption losses. As a result, the signal is almost intact when it reaches the fluid. Also, the preliminary focusing by the concave crystal and the second focusing by the conduit lens highly concentrates all that energy as it is sent across the flow. As a result of all this, the return signals are stronger, and particles as small as 0.4 micron will reflect enough energy to be detected by the crystal 16. The result is not entirely attributable to the additional concentration of the signal caused by the double focusing arrangement or by the reduction in energy loss alone. The returning signal is then counted by the receiver 50 and displayed on the oscilloscope, as in my U.S. Pat. No. 4,112,773. The sensitivity of the crystal 16 to reflected signals is enhanced because the two separate grounded shielding layers 24, 32 effectively isolate the crystal 16 from any extraneous noise signals from below.

It is also possible to eliminate the conduit lens and use the concave crystal as the sole focusing means. The signal from this arrangement would be highly concentrated, as it would be focused three-dimensionally.

OTHER EMBODIMENTS

In another preferred embodiment, the crystal is changed from a 7.5 MHz crystal to a 1.0 MHz crystal, and a decibel level detector 60 (shown in broken lines) is attached to the pulse generator 54. A Matec Model 2470A Attenuation Recorder is a suitable detector. Of course, other non-concave crystals such as those in my U.S. Pat. No. 4,112,773 may be used in this embodiment as well, because focusing and scattering effects are not as critical in determining the composition of a fluid containing no particles to be detected.

Figure 4:
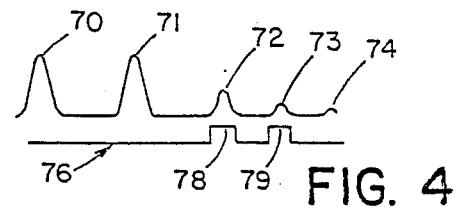
FIG. 4 is an echo waveform.
Figure 5:
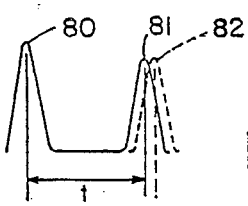
FIG. 5 is another echo waveform.

In this embodiment, the ultrasonic signal from the crystal bounces off and returns to the crystal from both the near wall and the far wall of the conduit 12. The returning signal has peaks 70, 71, as shown in FIG. 4. A portion of the original signal, however, continues to ring between the walls of the conduit 12 until it gradually dies out. These ringing signals are also detected by the crystal 16 and can be displayed on the oscilloscope 52 as secondary peaks 72, 73, 74. The higher the peak the more ultrasonic energy the returning signal contains. The oscilloscope's second trace 76 having boxes 78, 79 is then adjusted so that the boxes 78, 79 overlap two of the secondary peaks. The decibel level detector 60 then measures the decibel level dropoff between the peaks. This dropoff is directly proportional to the sound absorption capability of the fluid. As each liquid component of a fluid has a different sound absorption level, it is then possible to determine the relative percentages of components therein, even for a homogeneous fluid.

The amount of attenuation is recorded for a number of frequencies. In view of the rapid manner in which successive pulses may be sent, the attenuation measurements at different selected frequencies could be considered virtually instantaneous. Also, a single multi-frequency pulse could be used. Each chemical or liquid component has its own rate of sound absorption which may vary with frequency. For example, in one case the amount of absportion may increase as the frequency increases, while for another fluid the amount of absorption may rise and then fall with increasing frequency. The absorption of still others may decrease or not change at all as a function of increasing frequency. Accordingly, depending on the measured attenuation for the homogeneous fluid over a number of frequencies, a change in percentage of the composition can be detected, as the absorption will change.

Figure 6:
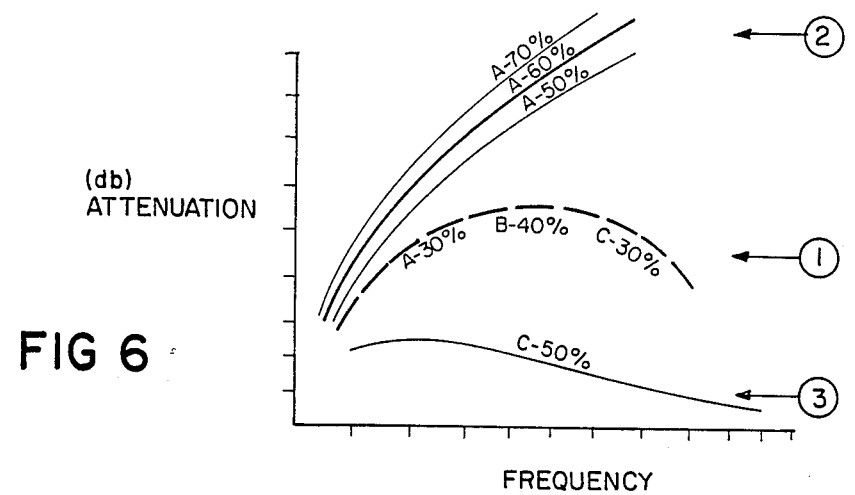
FIG. 6 is a graph of absorption v. frequency for a fluid with three components.

A simplified graph, which is merely representative and not a graph of an actual multi-component fluid, is shown in FIG. 6. There, plot number 1 represents the attenuation of the homogeneous fluid when the components A, B, C have the proper percentages. If the percentage of component A should increase, (the relative percentages of the other components remaining the same with respect to each other for this example) the attenuation readout becomes like that of plot number 2, with the specific attenuation at a given frequency changing somewhat with the percentage change of component A. Similarly, if component C should increase, the graph becomes like that of plot number 3. Thus, the attenuation measurement can be used in this manner to identify the component which has changed and the percentage of the change. A plot of attenuation versus frequency for any combination of percentages will in most multi-component fluids be different than that of all the other combinations, although some portions of some of the plots may have common points. Therefore, when the results of the actual attenuation versus frequency graph is compared with a prepared graph showing the plots of the fluid having different percentages of components, the component that has changed can be identified, and the percentage of the change determined. Also, a non-homogeneous fluid can be easily detected because the decibel level dropoff will fluctuate substantially. This method may be used with both a standing and a flowing fluid, and may even be used to monitor a changing chemical process, as long as the timing for the changes is known and the results of the changes can be plotted in advance for the purposes of comparison.

The velocity of sound is different for different liquids, and fluid information can also be obtained by measuring the sound velocity therein. The x-axis of the oscilloscope display is a function of time. Therefore, by displaying two main conduit echoes 80, 81 on the oscilloscope, the time between them can be easily determined. As the speed of sound diminishes, the second peak, such as a peak 82, moves farther away from the first peak 80. As before, if the fluid has a few known components, the speed of sound in the fluid can be used to determine the percentage of the components in the fluid.

Figure 7:
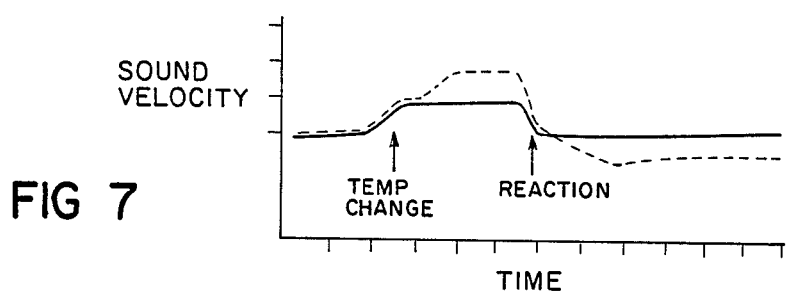
FIG. 7 is a graph of sound velocity v. time for multicomponent fluid.

For a given temperature and pressure, the velocity of sound through the composition will vary depending on changes in the percentage of the components, as the velocity of sound is usually different for different chemicals. If sound velocity is measured over a period of time, the only changes that should occur are because of chemical reactions in any ongoing process (e.g., the addition of a small amount of catalyst at a certain point so that two of the fluid components combine to form a third) or because of pressure or temperature changes. Otherwise, velocity change must be due to changes in the chemical composition of the fluid. Therefore, as shown in the graph of FIG. 7, the proper plot for the multi-component fluid is the solid line, and the dotted line represents the plot for the actual fluid. By determining the manner in which the velocity is above or below the proper plot, the component which has increased or decreased and the percentage can be determined, as the speed of sound will differ in each. As before, several percentages would change at once, but the overall graphs for each possible combination at different points (i.e., after a reaction etc.) would be sufficiently different in most cases to allow identification of which components had changed percentages and by how much. Similarly, a non-homogeneous flow can be detected because the speed of sound will fluctuate.

Figure 8:
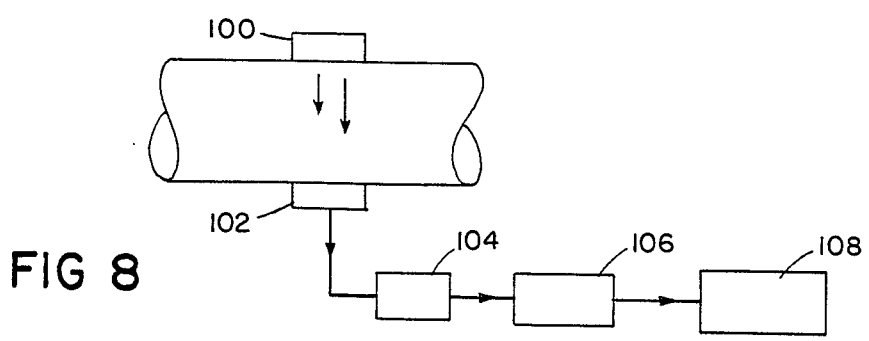
FIG. 8 is a block diagram of a system for determining fluid composition.

The composition of the homogeneous, multi-component fluid can also be determined by use of a fast Fourier transform on the pulses sent through the fluid to produce a frequency spectrum. As shown in FIG. 8, a pair of broadband transducers 100, 102 are disposed across from each other on opposite sides of a flow. Transmitting transducer 100 is connected to a Micro Pure 1150/812 Pulser. Receiving transducer 102 is connected to a receiver 104, which in turn is connected to an A to D converter 106 and a computer 108. The receiver is a Matec 625 Broadband receiver. The A to D converter is a Biomation 8100 A-D converter, and the computer 108 is a PDP 11/40.

Figure 9:
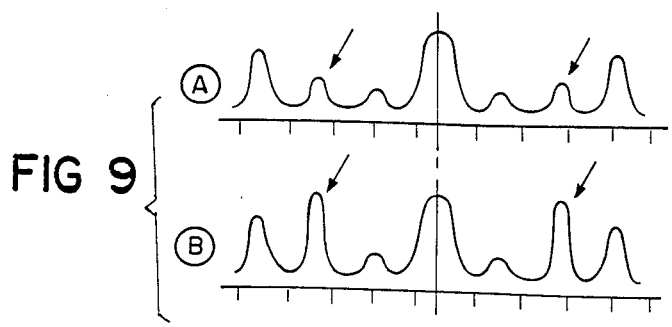
FIG. 9 is a pair of frequency spectra for a fluid with two slightly different compositions.

The pulse sent from transducer 100 to transducer 102 is detected and converted into a frequency spectrum in the same manner as with my U.S. patent application Ser. No. 151,834 filed May 21, 1980 now U.S. Pat. No. 4,339,944, also incorporated herein by reference. Two such spectra are shown in FIG. 9. If the percentage of a component changes, it will be reflected in an increase or a decrease in certain portions of the resulting frequency spectrum. For different components, different portions of the spectrum (corresponding to different frequences) will be affected, and the percentage of the change will be reflected in the amount the different portions change. For example, a comparison of the spectra A and B of FIG. 9 shows that the second peak from each end has increased in spectrum B. Only one of the components would effect this pair of peaks, because of the nature in which various ultrasonic pulse is attenuated at different frequencies for different fluids. The amount of change would be reflected by the amount of the change in the peaks. Different components changing percentage would affect a different peak or combination of peaks. Therefore, the specific changing component or components may be identified and the percentage change determined.

Other embodiments of the invention will occur to those skilled in the art.

What is claimed is:

1. An ultrasonic device for obtaining information about a fluid comprising:
   a transducer for producing energy waves,
   a first lens for focusing the energy waves and directing the narrowed, focused waves to a limited portion of a second lens, thereby reducing any scattering losses or noise due to said second lens,
   said second lens further focusing the energy waves and directing the results double-focused energy waves into the fluid,
   wherein said transducer has a wave-generating surface, said surface comprising said first lens, said second lens comprising a curved conduit wall.

2. The device of claim 1 wherein said surface is concave and focuses the energy waves three-dimensionally.

3. The device of claim 1 wherein said transducer is at least partially surrounded by and insulated from a first and a second electrically grounded shield, said first shield comprising a first layer of electrically conductive material covering a sidewall surrounding said transducer, said second shield comprising a second layer of electrically conductive material being separated from said first layer by a layer of non-conductive material, both of said shields being connected to separate grounds.

4. An ultrasonic device for obtaining information about a fluid comprising:

a transducer for producing energy waves,
said transducer being at least partially surrounded by a first and a second electrically-grounded shield, said first and second shields being separated by a layer of non-conductive material and connected to separate grounds.

* * * * *